United States Patent [19]

Sisti et al.

[11] 4,383,839
[45] May 17, 1983

[54] METHOD AND DEVICE FOR VAPORIZATION INJECTION OF A LIQUID SAMPLE FOR GAS CHROMATOGRAPHIC ANALYSIS

[75] Inventors: Giorgio Sisti, Milan; Mario Galli, Legnano, both of Italy; Sorin Trestianu, Brussels, Belgium

[73] Assignee: Carlo Erba Strumentazione S.p.A., Rodano, Italy

[21] Appl. No.: 318,907

[22] Filed: Nov. 6, 1981

[30] Foreign Application Priority Data

Nov. 6, 1980 [IT] Italy .................. 25818 A/80

[51] Int. Cl.³ ........................... B01D 15/08
[52] U.S. Cl. .......................... 55/67; 55/197
[58] Field of Search ..................... 55/197, 67

[56] References Cited

U.S. PATENT DOCUMENTS

| | | | |
|---|---|---|---|
| 2,841,005 | 7/1950 | Coggeshall | 55/197 X |
| 3,225,520 | 12/1965 | Burow | 55/197 X |
| 3,225,521 | 12/1965 | Burow | 55/197 X |
| 3,841,059 | 10/1974 | McCabe | 55/197 |
| 4,269,608 | 5/1981 | Sisti et al. | |

FOREIGN PATENT DOCUMENTS 2823445 12/1979 Fed. Rep. of Germany ........ 55/197

Primary Examiner—John Adee
Attorney, Agent, or Firm—Millen & White

[57] ABSTRACT

This invention relates to a method and a device for vaporization injection of a liquid sample in a gas chromatographic column housed in an oven comprising a direct on column injector suitable for injecting a liquid sample into the initial zone of a capillary column and capable of pneumatically sealing the injection port at the end of injection. Between the injector and the gas chromatographic column itself an uncoated capillary column length is provided in which vaporization of the injected sample occurs using heat from an oven housing said capillary column length, said oven being the same or separate from the oven containing said gas chromatographic column.

10 Claims, 3 Drawing Figures

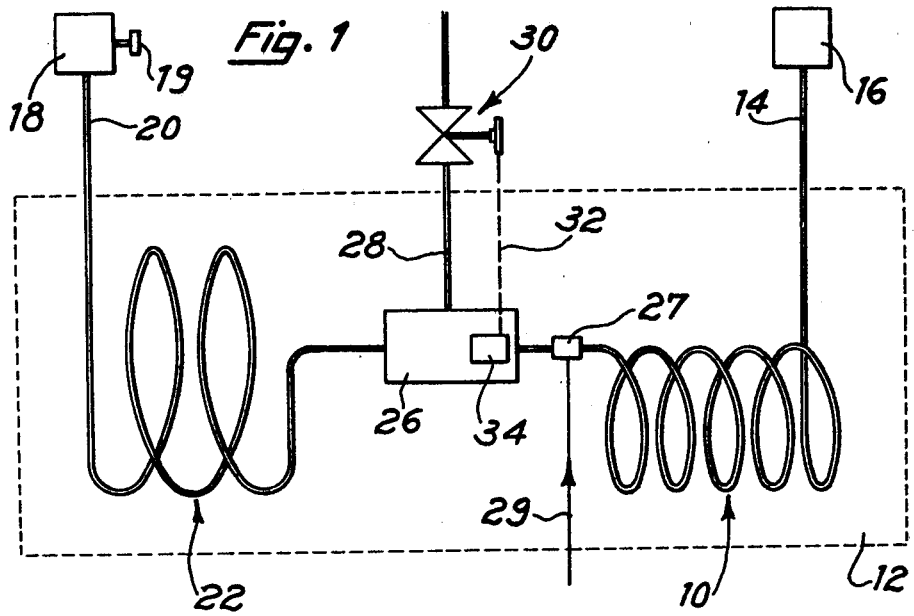
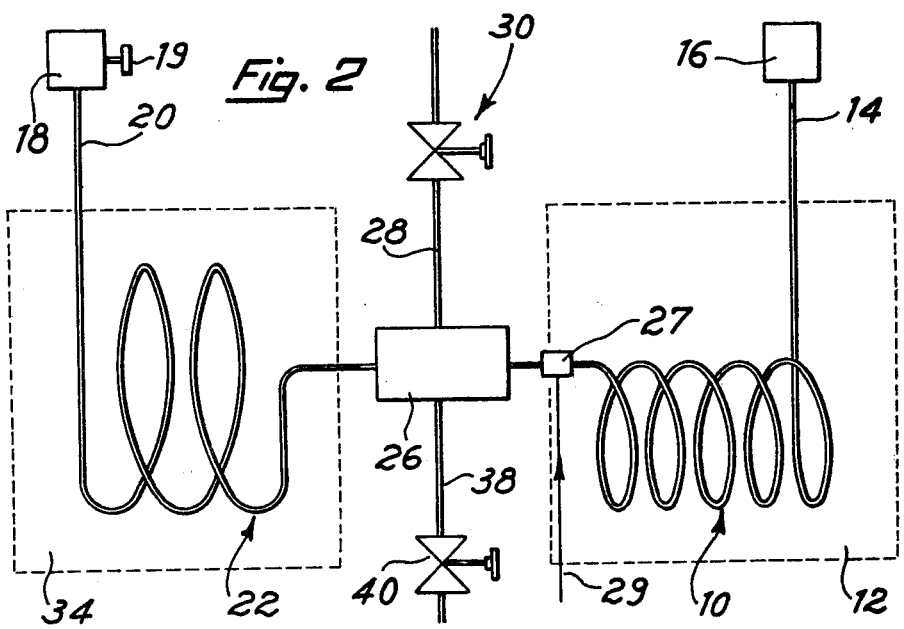
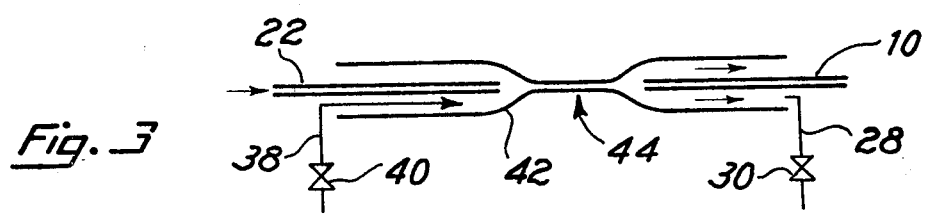

METHOD AND DEVICE FOR VAPORIZATION INJECTION OF A LIQUID SAMPLE FOR GAS CHROMATOGRAPHIC ANALYSIS

BACKGROUND OF THE INVENTION

1. Field of the Invention

This invention relates to a method and a device for vaporization injection in a gas chromatographic column.

2. Description of the Prior Art

In order to effect vaporization injection in gas chromatographic columns, so-called vaporization injectors are used, in which the liquid sample is vaporized by the high temperature of a chamber adjacent to the injector itself and wherein the sample is injected. After vaporization, the sample is sent to the gas chromatographic column by a carrier gas. However, the known vaporization injectors present many drawbacks, especially when the sample contains compounds having different volatility (volatile and high-boiling together) and thermolabile components. Other drawbacks of known vaporization injectors result from the need to have a suitably heated vaporization chamber and means to close said chamber on the sample injection side (in particular comprising a duct for an injection syringe needle) both during injection and at the end of same, and this above all when samples including a solvent, which has the tendency to quickly vaporize, are treated.

SUMMARY OF THE INVENTION

Accordingly, an object of this invention is to provide a method and a device wherein the problems and drawbacks of known vaporization injectors are completely avoided and wherein a perfect vaporization injection, with a consequently perfect analysis of the injected samples, is ensured. Essentially, according to the invention, said device comprises a direct on column injector, of the type suitable for directly injecting a liquid sample into the initial part of a capillary column, as well as section of capillary column which is not coated with stationary phase, placed upstream the gas chromatographic column and fed by said direct on-column injector, said section of capillary column being housed in an oven for heating and vaporizing the injected sample.

According to the present method, the injection is carried out with a liquid sample, which maintains its liquid condition during the whole injection stage inside the injector itself and in the initial part of said section of capillary column, and is vaporized only later, at the end of injection, when the oven is heated to cause vaporization and the subsequent beginning of separation of the sample components inside said section of capillary column.

Alternately, the oven can be kept at temperature, and in this case cooling of the injector and of the initial section of capillary column is carried out to keep the sample in a liquid condition.

When a splitting operation has to be foreseen, that is, an outlet discharge of part of the injected sample after vaporization thereof, so as to send only part of the injected sample into the gas chromatographic column, said splitting is carried out between said unocated section of capillary column and the gas chromatographic column, the splitting rate being controlled by suitable valves which are operated by a sensor detecting the oven temperature, in order to maintain the splitting ratio, e.g., the ratio between the sample flow sent to the gas chromatographic column and the sample flow upstream the splitting point, at a constant value while the temperature varies. Both in the previous case and in the case wherein said section of capillary column designed for sample vaporization is housed in a separate oven which is independently controlled with respect to the oven of the gas chromatographic column, it is advisable that, in the splitting zone between the two columns and upstream the splitting point, an additional flow of carrier gas is fed through a suitable line (make-up line), in order to obtain a mixing as homogeneous as possible of said carrier with the flow coming out of the vaporization column. In fact, thanks to said additional carrier flow, which can be adjusted, it is possible to control the time the sample remains inside the vaporization capillary column independently of the splitting ratio, while without said make-up line the residence time of sample in the vaporization column would depend upon the splitting ratio and would be lowest when the splitting ratio is highest. Furthermore, a suitable regulation of the flowrate in the make-up line to obtain the optimum sample residence time, provides a further advantage, in that a relatively reduced band width of the sample is achieved, both in the vaporization capillary column section and in the gas chromatographic column. If, despite this, the band width of the sample is still too wide, it is advisable to insert, upstream the chromatographic column, a trap for carrying out a sample re-concentration.

BRIEF DESCRIPTION OF THE DRAWINGS

FIG. 1 is a diagrammatic view of a first embodiment of the invention.

FIG. 2 is a diagrammatic view of a second embodiment, with separate ovens.

FIG. 3 is a diagrammatic view of means conveying additional carrier gas and of splitting means.

DESCRIPTION OF THE PREFERRED EMBODIMENTS

Referring to FIG. 1, a gas chromatographic column 10 is housed in an oven 12 and the outlet 14 of the column is connected to a detector 16 for analysis of the injected samples. The samples (comprising their solvents) are introduced by means of a direct on column injector 18 (which is known per se) positioned outside the oven and having a valve 19 acting on a duct in which the needle of an injection syringe is inserted, said needle injecting the liquid sample into the initial part of a capillary column 20, which extends, as indicated by reference 22, inside the oven 12. The capillary column 22 and the gas chromatographic column 10 are connected through a splitting device 26 having splitting duct 28 for discharging a given amount of the sample before analysis. Reference 27 indicates a so-called cool "trap", which is cooled through a line 29, appertaining to the column 10 itself or in the form of an independent element placed between the column and splitting device 26. The splitting flow, which is usually a very high percentage of the sample injected into column, is controlled by means of a valve device 30, which in turn can be advantageously controlled, through a connection 32, by a detector 34 of the oven temperature, in order to maintain a constant splitting ratio notwithstanding temperature variations. To perform a gas chromatographic analysis in the case of the embodiment of FIG. 1, the valve 19 of injector 18 is opened and the liquid sample is injected into the initial length of the capillary column 22. No vaporization occurs because the oven 12 is kept cold, or because the injector and the first length of column are cooled (secondary cooling). Once the injection is carried out and the valve 19 is closed, vaporization is performed or completed.

After vaporization, splitting takes place at 26 with a splitting ratio depending on the concentration and other features of the sample. The trap 27 can be actuated, in case it is necessary or advisable to decrease the band amplitude of the sample before it enters the gas chromatographic column.

Another embodiment of the invention is illustrated in FIG. 2, where the same components as in FIG. 1 are indicated by the same reference numerals. This embodiment differs from the previous one in that the capillary column 22 is housed in its own oven 36, independent from the oven 12 of the gas chromatographic column 10, said oven 36 being controlled independently from oven 12.

Communicating with the splitting zone 26, between said two ovens 12 and 36, a so called make-up line 38 is also provided, which controls the introduction of a further flow of carrier gas through a flow regulating valve 40, immediately upstream the splitting point. A similar make-up line can also be provided in the splitting device 26 of FIG. 1.

This carrier gas feeding can be effected in any way, provided that, before the splitting outlet, the entering carrier gas is mixed as homogeneously as possible with the flow coming out from the vaporization column.

This is in particular obtained with the embodiment of FIG. 3, where a venturi-shaped tube 42 is used, in the narrow zone 44 of which a mixing of the injected and vaporized sample coming from column 22 and of the carrier flow of make-up line 38 is carried out. Downstream said section 44, the sample is partly fed to the chromatographic column 10 and partly discharged into the splitting line 28.

As mentioned, said make-up line makes it possible to obtain, by a regulation of the carrier flowing through valve 40, an optimum residence time of sample in the column 22, in relation to the sample nature (specially its volatility) and the temperature of oven 36, and this independently from the splitting ratio, which can be separately regulated (by means of valve 30), on the basis of other sample features. It must be noted that as the capillary column 22 can perform sample vaporization even gradually, the splitting operation in this case, as well as in the case of the previously described embodiment, goes on during the whole analysis and is not limited to the sample injection stage, as, on the contrary, is usually the case when conventional vaporization injectors are used.

The shown embodiments can undergo several modifications, without departing from the spirit and scope of the present invention.

We claim:

1. A device for effecting controlled vaporization injection of a liquid sample for gas chromatographic analysis, comprising:
a vaporization tube provided with temperature control means for maintaining an injected sample in the liquid state until injection is complete and then effecting controlled heating and vaporization of the sample, said tube being adapted to communicate at its upstream end, through a closable valve, with injection means, and at its downstream end, through sample splitting means, with a chromatographic column containing a stationary liquid phase for gas chromatographic separation of the vaporized sample exiting the vaporization tube;
injection means communicating through said valve with the upstream end of said vaporization tube, for direct injection of a liquid sample into an initial zone of said tube, and provided with valve means for closing off said injection means following injection of said sample into said tube; and
sample splitting means communicating with the downstream end of said vaporization tube and with the upstream end of said chromatographic column, for splitting said vaporized sample and diverting a portion thereof from said column, said splitting means being provided with valve means for controlling the splitting ratio.

2. A device according to claim 1, wherein said splitting control valve means are in turn controlled in relation to the oven temperature to obtain a constant splitting ratio, being the ratio of the flow sent to the chromatographic column compared to the total flow upstream the splitting point.

3. A device according to claim 1, wherein said vaporization tube is housed in a separate oven which is submitted to a temperature variation program independent from that of the oven containing said gas chromatographic column.

4. A device according to claim 1, wherein said means further comprises means, upstream the splitting point, for providing an adjustable make-up flow of carrier gas for mixing with the sample flow exiting the vaporization tube.

5. A device according to claim 4, which further comprises means for rapidly and homogeneously mixing said make-up flow and said sample flow.

6. A device according to claim 5, wherein said mixing means comprises a Venturi-shaped tube having a central, reduced-diameter mixing zone, a zone upstream said reduced diameter zone which is wider than and coaxial with the outlet of said vaporization tube and which receives said make-up flow, and a zone downstream said reduced diameter zone which is wider than and coaxial with the inlet end of said chromatographic column and through which is diverted said diverted portion of the sample.

7. A device according to claim 1, which further comprises a cooling trap at the inlet end of said gas chromatographic column for concentrating the sample.

8. A method for effecting controlled vaporization injection of a liquid sample for gas chromatographic analysis, comprising the steps of:
injecting a liquid sample into the initial zone of a sample vaporization tube which does not contain stationary liquid phase, the sample being maintained in the liquid phase during substantially the entire injection process;
heating the vaporization tube to vaporize the sample, and passing a carrier gas therethrough to entrain the vaporized sample; and
diverting a portion of the resultant mixture of vaporized sample and carrier gas by means of a sample splitter, and conducting the remainder to a chromatographic column containing a stationary liquid phase for chromatographic separation, while maintaining a substantially constant splitting ratio, being the ratio of said remainder which is sent to the chromatographic column compared to the total mixture, by controlling the amount of diverted mixture as a function of the temperature of the heated vaporization tube.

9. A method according to claim 8, which further comprises providing a regulatable make-up flow of carrier gas to the sample splitter, upstream the splitting point; homogeneously mixing said make-up flow with the sample flow exiting the vaporization tube upstream the splitter; and regulating the make-up gas flow rate and the temperature of the vaporization tube to minimize the sample band width.

10. A method according to claim 9, wherein said homogeneous mixing is effected by passing the mixture of vaporized sample and carrier gas into a Venturi-shaped tube having a central, reduced-diameter mixing zone and wider ends, the upstream end being wider than and coaxial with the outlet of the vaporization tube, said upstream end also receiving the make-up gas flow, and the downstream end being wider than and coaxial with the inlet end of the chromatographic column, said downstream end being provided with means to divert said diverted portion of the mixture of sample and carrier gas, the remainder passing into said column.

* * * * *